United States Patent [19]

Lowe et al.

[11] Patent Number: 5,277,912
[45] Date of Patent: Jan. 11, 1994

[54] SUSTAINED RELEASE CAPSULE AND FORMULATIONS

[75] Inventors: Lionel B. Lowe; Colin J. McArthur, both of New South Wales, Australia

[73] Assignee: Eli Lilly and Company, Indianapolis, Ind.

[21] Appl. No.: 863,898

[22] Filed: Apr. 6, 1992

[30] Foreign Application Priority Data

Apr. 5, 1991 [AU] Australia ............................. PK5490
Sep. 16, 1991 [AU] Australia ............................. PK8394

[51] Int. Cl.$^5$ .............................................. A23K 1/18
[52] U.S. Cl. ...................................... 424/438; 604/57; 604/890.1; 604/892.1
[58] Field of Search ..................... 424/438; 604/890.1, 604/892.1, 57

[56] References Cited

U.S. PATENT DOCUMENTS

| | | | |
|---|---|---|---|
| 4,312,347 | 1/1982 | Magoon et al. | 128/260 |
| 4,381,780 | 5/1983 | Holloway | 604/892 |
| 4,416,659 | 11/1983 | Simpson | 604/57 |
| 4,439,197 | 3/1984 | Honda et al. | 604/891 |
| 4,671,789 | 6/1987 | Laby | 604/59 |
| 4,717,718 | 1/1988 | Eckenhoff et al. | 514/30 |
| 4,867,980 | 9/1989 | Edwards et al. | 424/438 |
| 4,929,233 | 5/1990 | Roth | 604/892.1 |

FOREIGN PATENT DOCUMENTS

| | | |
|---|---|---|
| 1163983 | 8/1983 | Australia . |
| 3728185 | 7/1985 | Australia . |
| 4308285 | 12/1985 | Australia . |
| 7925587 | 4/1988 | Australia . |
| 4708989 | 6/1990 | Australia . |
| 0061783 | 10/1982 | European Pat. Off. . |
| 0062391 | 10/1982 | European Pat. Off. . |
| 0079724 | 5/1983 | European Pat. Off. . |
| 8200094 | 1/1982 | PCT Int'l Appl. . |

*Primary Examiner*—Thurman K. Page
*Assistant Examiner*—D. Gabrielle Phelan
*Attorney, Agent, or Firm*—Woodard, Emhardt, Naughton, Moriarty & McNett

[57] ABSTRACT

A sustained release capsule adapted to be inserted into the rumen of a ruminant animal and means for retention of the capsule in the rumen. A sustained release capsule adapted to be inserted into the rumen of a ruminant animal through its oesophagus and retained within the rumen over a prolonged period to continuously deliver a biologically active composition carried in the capsule, comprising an elongated tubular body comprising a tube and an end cap secured to one end thereof for substantially enclosing the biologically active composition, the other end of the capsule being a delivery end, the body having an opening at the delivery end of the capsule for delivery of the composition to the rumen, and a plurality of retention arms attached to or formed integrally with the cap, the arms being adapted to extend outwardly from the cap for retaining the capsule in the rumen, the arms being resilient to enable them to bend from their outwardly extending positions toward the body so that they lie alongside the body allowing the capsule to be inserted through the animal's oesophagus, the resilient arms normally extending from the body at an angle between 75° and 90° with respect to the axis of the tubular body, and for each arm said cap has an external curved surface disposed with respect to the arm so that when the arm is bent toward the body, the arm contacts the curved surface and the curved surface controls the bending of the arm so that the arm does not bend abruptly, said arms being adapted to return to their outwardly extending positions when the capsule reaches the rumen, characterized in that said cap is secured to said one end by means of at least two circumferential beads having at least one sealing ring located therebetween.

29 Claims, 6 Drawing Sheets

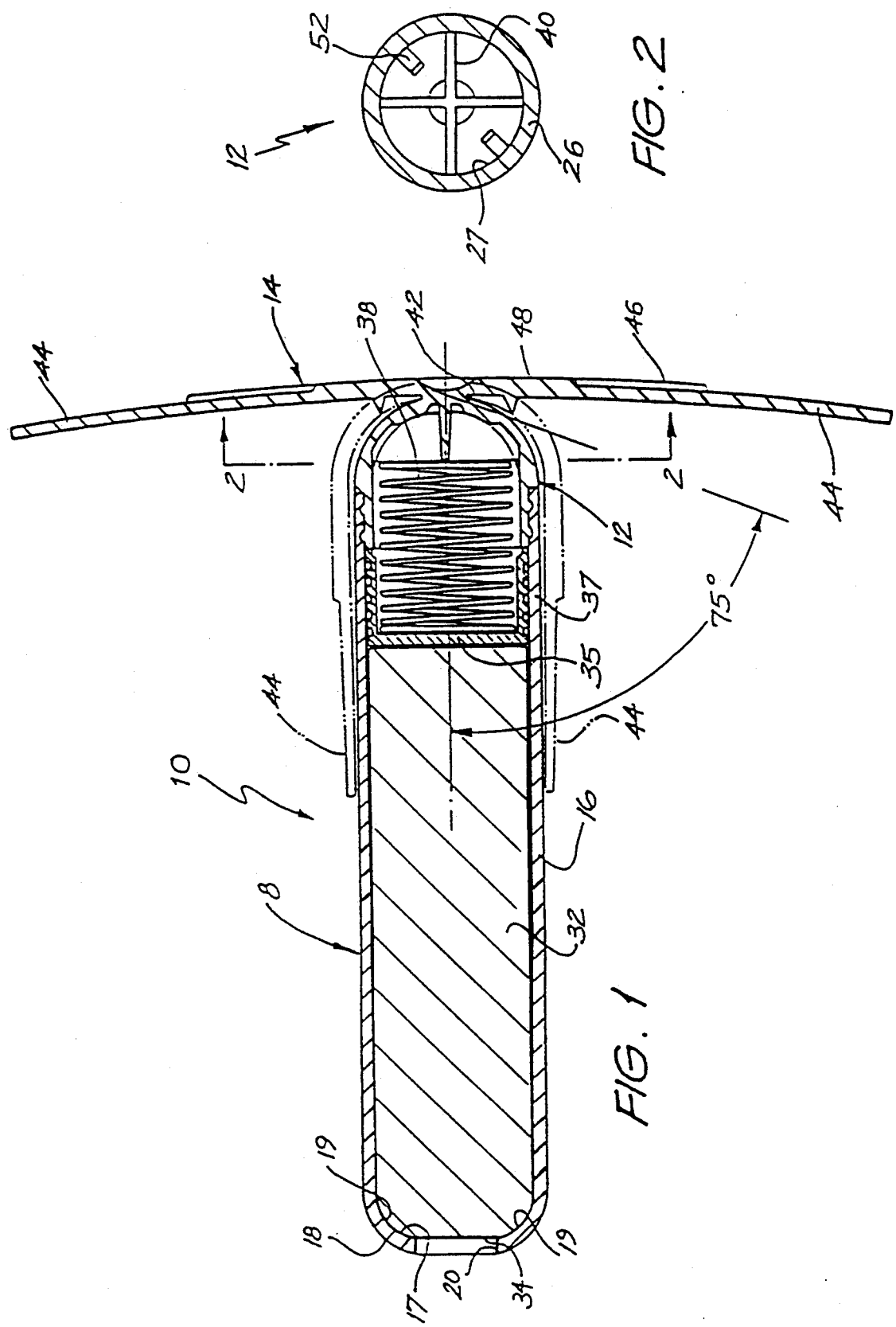

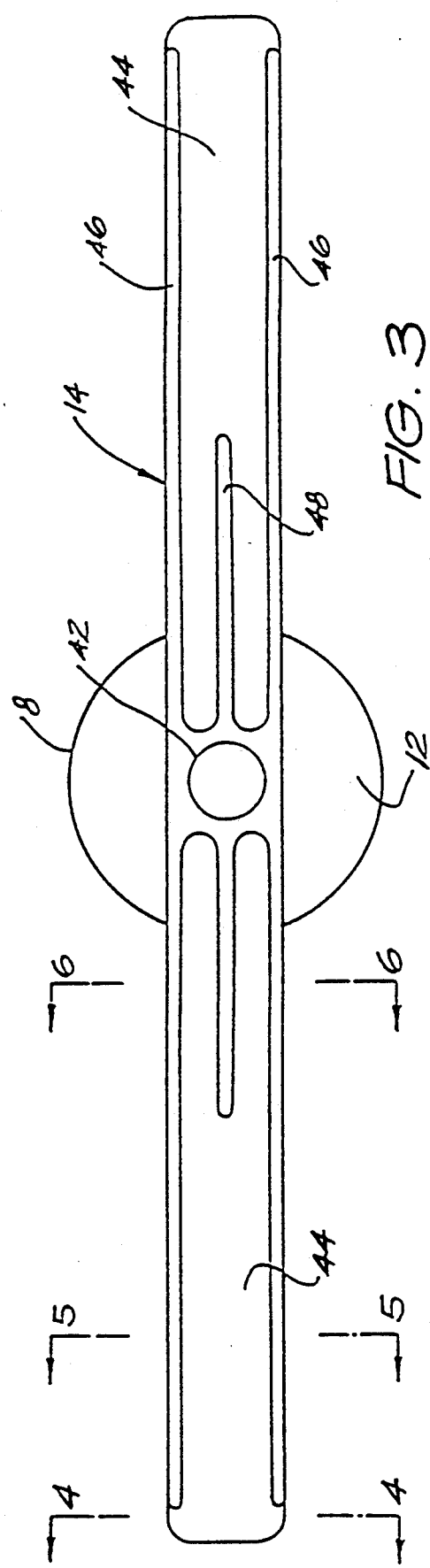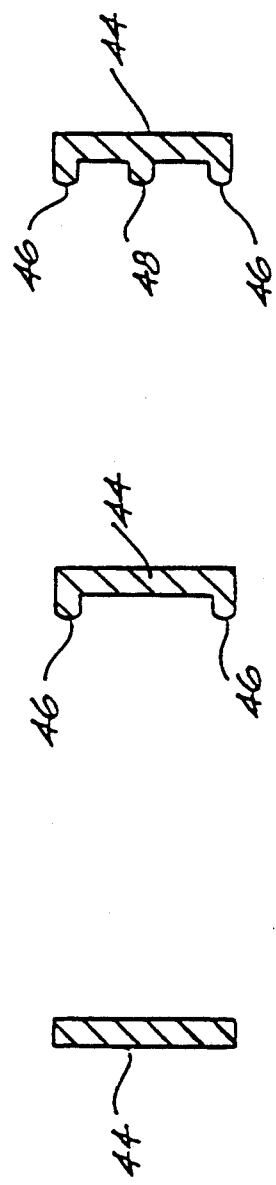

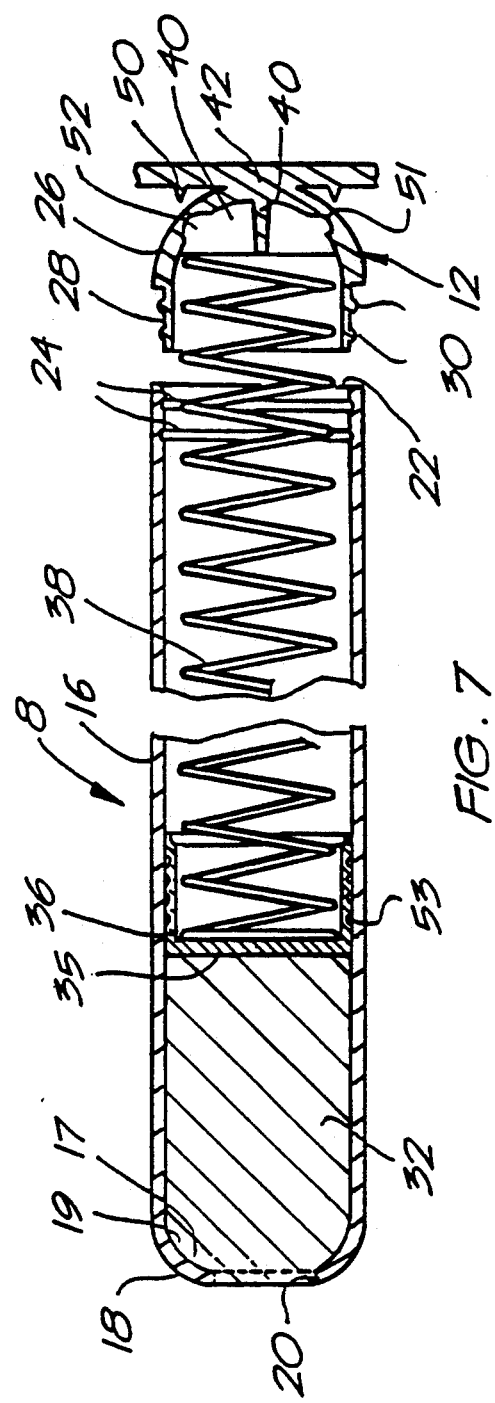

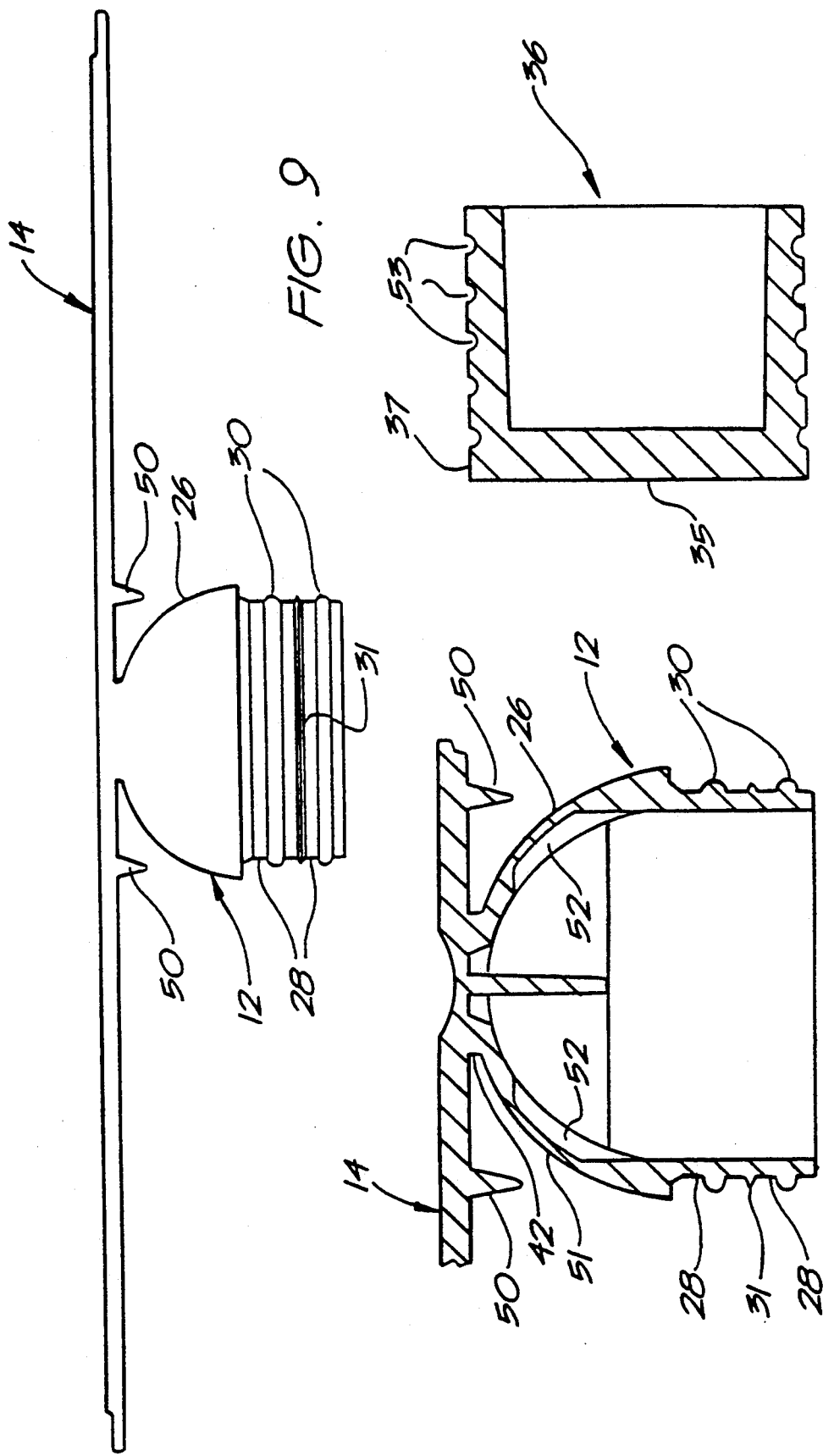

SUSTAINED RELEASE CAPSULE AND FORMULATIONS

TECHNICAL FIELD

This invention relates to a sustained release capsule adapted to be inserted into the rumen of a ruminant animal through the animal's oesophagus and to be retained in the rumen over a prolonged period to continuously deliver a biologically active agent or composition carried in the capsule.

BACKGROUND ART

A device which is currently available is characterized by a capsule comprising a hollow tubular body having an opening at one end, a plunger driven by a spring for urging a solid therapeutic composition contained in the body towards the opening, an annular flange around the opening to prevent the driving means for expelling the solid composition from the body, and two resilient arms which are attached to a cap which seals the tubular body of the other end.

A difficulty with the present device is that the cap is welded onto the hollow body. The welding is often not efficient and allows entry of water and ruminal fluid into the capsule. The therapeutic composition is usually a hygroscopic composition and in the presence of water swells and eventually ruptures the capsule. Poor welding can also result in capsule rupture which is not desirable because the sudden release of the whole of the therapeutic composition intended for sustained release can cause death of the animal.

Another difficulty is the inclusion of vent holes in the cap. The vent holes are needed so that a vacuum will not form when the capsule is administered. Prior to and during administration of the capsule, the lubricant has a tendency to leak through the vent holes. Loss of lubricant from the vent holes is not desirable. The lubricant acts as a seal and provides a barrier film. Any loss of lubricant could result in erratic payout of the therapeutic composition.

Another difficulty with the present device is that the flanged edge of the piston provides a poor seal. The poor sealing results in water entering the capsule thereby causing friction as the piston moves along the tube. This friction is responsible for erratic payout of the therapeutic composition. Furthermore piston failure will result in water entering the capsule to cause swelling of the therapeutic composition and increased friction.

There is need for a sustained release capsule which can effectively remain sealed throughout the retention time in the rumen. There is also a need for a sustained release capsule which can continuously deliver a therapeutic or growth stimulating composition to range-fed ruminants, such as cattle or sheep.

OBJECT OF INVENTION

It is an object of this invention to provide a sustained release capsule with improved sealing and an easier flowing piston to give continuous release of therapeutic composition from the capsule.

DISCLOSURE OF INVENTION

According to a first embodiment of this invention there is provided a capsule for administering a composition to a ruminant animal comprising a body having a barrel, and a cap, the cap and barrel each having cylindrical portions which nest one within the other to form a sealed closure, one of the portions having spaced apart annular grooves formed therein, the other cylindrical portion having similarly spaced apart circumferential beads which fit within the grooves, one of the portions also comprising a circumferential sealing ring.

According to a second embodiment of this invention there is provided a device for administering a composition to a ruminant animal comprising a sealed capsule having located on an exterior surface at least one resilient retention arm, the retention arm comprising a protrusion formed on a surface of the arm facing the capsule, the arm adapted to flex such that the protrusion contacts a portion of the capsule, said portion penetrable by the protrusion to form a vent.

According to a third embodiment of this invention there is provided a capsule for administering a composition to a ruminant animal comprising a cylindrical barrel having at one end a discharge opening and having the composition located between a piston and the opening, the piston biased toward the opening by a spring, the piston having one or more grooves formed circumferentially around an outer surface.

According to a fourth embodiment of this invention there is provided a device for administering a composition to a ruminant animal comprising a cylindrical capsule having a discharge opening at one end and generally closed at the other end, a piston located within the body, the piston urged toward the discharge opening by a roll spring, one end of the spring impinging onto the piston, the other end of the spring impinging on a rim of a thimble, the thimble comprising a cylindrical center portion, tapered at one end and having the rim formed around the other end, the rounded end of the thimble inserted into the spring and having the rim interposed between the spring and the closed end of the capsule.

According to a fifth embodiment of this invention there is provided a method of assembling a two-part capsule for administering a composition to a ruminant animal comprising the steps of loading a first part of the capsule with the composition, inserting a piston into the leaded capsule part, inserting a thimble into an outer end of a coil spring, the thimble comprising a body, rounded at one end and having a rim at the other, the rounded end and body located within the spring, the rim impinging on the outer end, inserting an inner end of the spring within the first part and onto the piston, fitting a second part of the capsule into sealing engagement with the first part and in doing so compressing the spring so that a portion of the spring coils about the body.

According to a sixth embodiment of this invention there is provided a sustained release capsule adapted to be inserted into the rumen of a ruminant animal through its oesophagus and retained within the rumen over a prolonged period to continuously deliver a biologically active composition carried in the capsule, comprising an elongated tubular body comprising a tube and an end cap secured to one end thereof for substantially enclosing the biologically active composition, the other end of the capsule being a delivery end, the body having an opening at the delivery end of the capsule for delivery of the composition to the rumen, and a plurality of retention arms attached to or formed integrally with the cap, the arms being adapted to extend outwardly from the cap for retaining the capsule in the rumen, the arms being resilient to enable them to bend from their outwardly extending positions toward the body so that they lie alongside the body allowing the capsule to be inserted through the animal's oesophagus, the resilient arms normally extending from the body at an angle between 75° and 90° with respect to the axis of the tubular body, and for each arm said cap has an external curved surface disposed with respect to the arm so that when the arm is bent toward the body, the arm contacts the curved surface and the curved surface controls the bending of the arm so that the arm does not bend abruptly, said arms being adapted to return to their outwardly extending positions when the capsule reaches the rumen, characterized in that said cap is secured to said one end by means of at least two circumferential beads having at least one sealing ring located therebetween.

The tubular body of the capsule may contain a labyrinth piston surrounded by lubricant and means for biasing the piston toward the delivery end for moving a supply of active composition toward the delivery opening when the capsule is in use.

Preferably the piston is adapted to move in slidable sealed relation in the body to restrict access of ruminal fluid to the supply of active composition other than at the delivery opening.

Generally the cap has at least one area of reduced thickness and the arms have at least one protrusion on the side adjacent the cap corresponding so that when the arms are urged alongside the body, the protrusion(s) engage and cause rupture(s) of the wall of the cap at said at least one area thereby providing at least one vent to relieve any vacuum formed on movement of the piston.

The invention solves the problem of how to provide sustained release capsules with more dependable sealing means. It does this by providing an improved means of preventing ruminal fluid from contacting the plug of composition at areas other than the discharge opening. As the composition is delivered, and the remaining plug of composition is urged toward the delivery opening, the space behind the plug within the capsule tends to fill with ruminal fluid, which can swell or erode the plug within the capsule.

Preferred embodiments of the present invention solve this problem, and thereby provides better control of administration with more uniform delivery over long periods. More particularly, in certain preferred embodiments of the invention the delivery opening in the tubular body of the capsule is surrounded by a circumferentially continuous frustoconical surface against which the plug of composition within the capsule is urged into sealing relation.

In a preferred embodiment of the invention a labyrinth piston urges the plug of composition toward the opening and moves in sealing relation with respect to the inner walls of the body. Lubricant fills the grooves of the piston and allows the piston to move toward the opening without friction. Lack of friction prevents erratic payout of the therapeutic composition.

In another preferred embodiment the presence of protrusions on the arms of the capsule rupture thin sections of the wall of the cap to produce vents. During administration of this preferred capsule, the protrusions seal the vents thereby preventing leakage of lubricant. When the capsule is located in the rumen, the arms elongate thereby releasing the protrusions from the vents so that the formation of a vacuum is prevented.

In another preferred embodiment, when the biasing means is a coiled spring, the spring can be prevented from twisting by locating a thimble within the spring.

Active ingredients which may be used in the capsules of the invention include any active ingredient which is suitable for administration to a ruminant animal. Preferred are those which are desirably administered directly into the rumen.

Suitable active ingredients include polyether antibiotics or ionophores, glycopeptide antibiotics anthelmintics and endectoparasiticides.

Polyether antibiotics or ionophores are useful as growth promotants, milk production enhancers and as therapeutic agents for the treatment of bloat. The polyether antibiotics which can be employed include those produced by the Streptomyces genus of micro organisms. They are characterized by comprising a multiplicity of cyclic ethers in their structures. The class is reviewed in *Kirk-Othmer: Encyclopedia of Chemical Technology*, Vol. 3, Third Edition (John Wiley & Sons, 1978), Page 47 et seq.; in *Annual Reports in Medical Chemistry* Volume 10 (Academic Press, N.Y. 1878), page 246 et seq.; and in J. Chrom. Lib., Volume 15 (Elsevier Scientific Publishing Co., N.Y. 1978), page 488 et seq.

Representative of the polyether antibiotics to be employed in the combination of this invention include ruminal propionate enhancers such as monensin (including the various factors A, B, and C, and the alkali metal salts, for instance monensin sodium, and the various esters thereof), ionomycin, laidlomycin, nigericin, grisorixin, dianemycin, Compound 51,532, lenoremycin, salinomycin, narasin, lonomycin, antibiotic X206, alborixin, septamycin, antibiotic A204, Compound 47,224, etheromycin, lasalocid (factors A, B, C, D, and E), mutalomycin, K41, isolasalocid A, lysocellin, tetronasin, and antibiotics X-14766A, A23187 and A32887.

Preferred polyether antibiotics include monensin, narasin, lasalocid, salinomycin, A-204, lonomycin, X-206, nigericin, and dianemycin, and especially monensin, narasin, lasalocid and salinomycin.

An especially preferred polyether to be utilised according to this invention is monensin, a compound widely used in the improvement of feed utilisation in ruminants (see U.S. Pat. No. 3,839,557). As used herein, "monensin" includes the various active factors, the salts such as monensin sodium, and the monensin esters such as carbamate esters and the like.

Glycopeptide antibiotics are also useful as growth promotants, milk production enhancers and as therapeutic agents for the treatment of bloat. They may be used alone or in combination with the polyether antibiotics as described in Australian Patent 556 299.

Typical of such glycopeptide feed utilisation efficiency enhancers are actaplanin, avoparcin, A35512, A477, ristocetin, vancomycin, and related glycopeptides.

Preferred glycopeptides to be employed in the combinations of this invention include actaplanin, avoparcin, ristocetin, and vancomycin.

Anthelmintics may be used for the treatment of blood flukes, flukes that live in the lungs, the liver, the intestines, tapeworms, intestinal roundworms, roundworms of blood and tissues, or combinations thereof. Preferred anthelmintics include antimony potassium tartrate, bephenium hydroxy naphthoate, bithionol, chloroquine, dichlorophen, diethylcarbamazine citrate, hexylresorcinol, hycanthone mesylate, lucanthone hydrochloride, mebendazole, niclosamide, niridazole, piperazine citrate, pyrantel pamoate, pyrvinium pamoate, quinacrine hydrochloride, stibocaptate, stibophen, tetrachloroethylene, thiabendazole, phenothiazine, hexachloroethane, carbon disulphide or benzimidazole. An especially preferred anthelmintic is benzimidazole. Examples of suitable benzimidazoles include thiabendazole, albendazole, cambendazole, fenbendazole, mebendazole, oxfendazole, and oxibendazole.

Preferred endectoparasiticides include organo phosphates and carbamates, avermectins, levamisole or sodium thiacetarsamide.

The activity of the active ingredients including the polyether antibiotics and/or the glycopeptide antibiotics may be enhanced by including in the formulations, one or more non ionic surfactants. Preferred surfactants are alcohol ethoxylates. Generally the ethoxylates are of octyl-, nonyl- and dodecyl phenol, natural and synthetic alcohols, saturated and unsaturated fatty acids and both block and random copolymers. Alcohol ethoxylates such as those of the Teric ® series or the Pluronic ® PE series or mixtures thereof are preferred. An especially preferred non ionic surfactant is Teric ® 12A23, which is lauryl (dodecanol) condensed with 23 moles of ethylene oxide.

Silicone anti foam agents may also be included in the formulations to enhance performance. The silicone anti foam agents may be aqueous or anhydrous, preferably anhydrous. The silicone anti foam agents may be a mixture of dimethyl silicones, such as those of Gensil ® series or the Rhodorsil ® series. Especially preferred silicone anti foam agents are Gensil ® 800 or Silbione ® 70 451.

The formulations may also include emulsifying agents or stabilisers. Preferred emulsifying agents or stabilisers include glycerol ester, glyceryl monostearate, hexaglycerol distearate, triglyceryl monostearate, decaglyceryl dipalmitate, sorbitan esters such as, sorbitan monostearate, sorbitan tristearate or ethoxylated esters such as glyceryl monolaurate, or mixtures thereof.

A typical formulation contains:
Surfactant: 50%
Monensin: 40%
Glycerol ester: 10%.
If an anti foam agent is included a typical formulation is:
Anti foam: 10%
Monensin: 40%
Glycerol ester: 50%.

BRIEF DESCRIPTION OF DRAWINGS

A preferred form of the present invention will now be described by way of example with reference to the accompanying drawings, wherein:

FIG. 1 is a substantially full-scale longitudinal section of a capsule in accordance with the invention, with the arms of the retention wing shown in full lines in their normal extended positions and shown in dotted lines in their folded administration positions for insertion of the capsule through an oesophagus;

FIG. 2 is a section taken on the line 2—2 of FIG. 1;

FIG. 3 is a front elevation of the wing and forward end of the capsule;

FIGS. 4, 5, and 6 are sectional views taken on the lines 4—4, 5—5, and 6—6 of FIG. 3;

FIG. 7 is a longitudinal section like FIG. 1, but on an enlarged scale and with a mid-portion of the barrel omitted and with the parts at the forward end of the capsule in partially exploded relation;

FIG. 9 is a side view of the wing and forward end of the capsule;

FIG. 10 is a side view of the cap;

FIG. 11 is a side view of the piston; and

BEST MODE(S) FOR CARRYING OUT THE INVENTION

Figure 8:
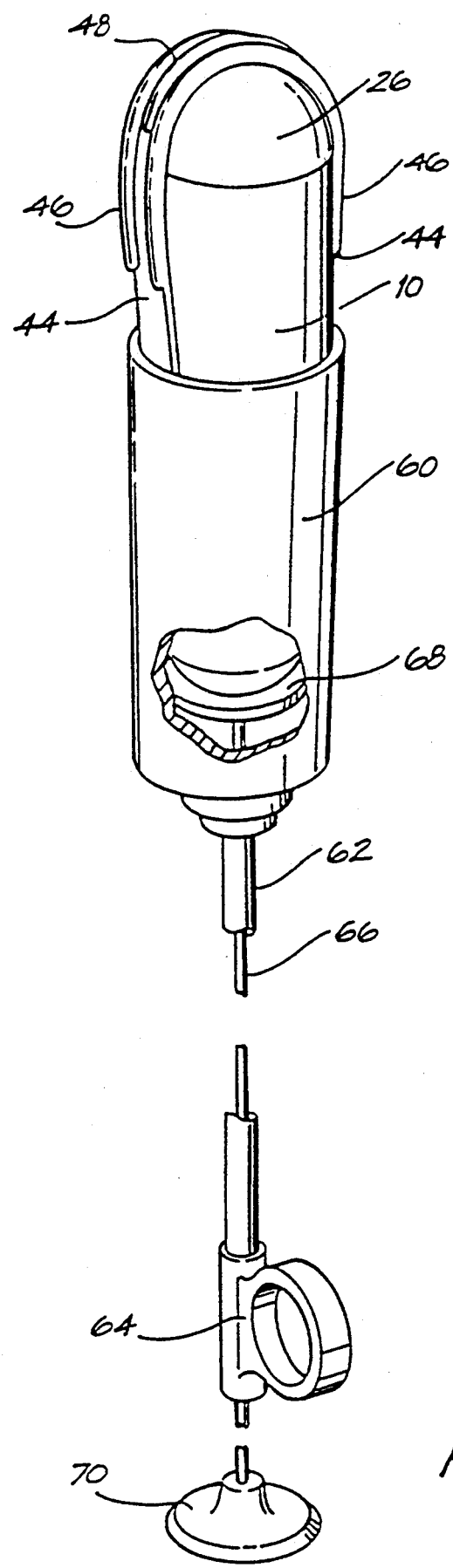
FIG. 8 is a diagrammatic view of an administration tool for inserting a capsule by mouth into the oesophagus of a bovine animal.

FIGS. 1-7 show a sustained release capsule 8 comprising a tubular body 10 adapted to enclose a solid core or plug of a biologically active composition 32. The body 10 has a generally cylindrical barrel or tube 16 joined in a smooth curve to an end wall or end 18 at the delivery end of the capsule. The barrel or tube has a cylindrical portion. To permit controlled access of ruminal fluid to the composition carried in the capsule, the end wall or end 18 has a constricted circular discharge opening 20. To urge the core or composition 32 toward the discharge opening 20 and thereby maintain a supply of composition at the delivery opening over a prolonged period, a piston 36 is provided in the capsule, which is urged against the core or composition 32 and toward the opening 20 by a biasing means such as a light coil spring 38.

To maintain sealing engagement between the core or composition 32 and the end wall or end 18 and thereby control access of ruminal fluid to the composition, the end wall is formed with a delivery opening. The inner face 17 merges at its periphery with a smoothly curved border surface 19. The charge or core of biologically active composition 32 is adapted to be weakened adjacent its end surface 34 by exposure through the delivery opening 20 to ruminal fluid. The border surface 19 serves to make initial sealing contact with the end edges of a pre-formed core of composition, and during use to maintain that peripheral seal and to guide the edge portions of the charge inward toward the delivery opening. The width of the surface 17 engaged by the weakened end of the charge and the solubility or flow characteristics of the charge may be varied to control the rate of progression of the administrative charge toward the delivery opening 20 and thereby to control the rate of delivery of the administrative composition from the capsule. The inner end of the charge may be protected from exposure to ruminal fluid, as by sealing the end of the capsule opposite the end having the discharge opening or by using a sealing piston, which will be described hereinafter in greater detail.

To retain the capsule in the rumen of an animal to which the capsule has been administered, the capsule is provided with a plurality of retention arms 44. As illustrated and as preferred, the arms 44 are connected to the tubular body at the end opposite the delivery end, which is sometimes referred to herein as the forward end. In the embodiments shown in the Figures, the two arms provided are substantially continuous; and form a wing 14.

To control the bending of the retention arms where they are attached to the tubular body and to thereby reduce the stress to which the arms are subjected, the body has curved surfaces 26 (FIG. 9) disposed with respect to the arms so that when an arm is bent toward the body, the arm contacts a curved surface 26, thereby causing the arm to bend over a long arc instead of abruptly at the point of attachment. In the illustrated embodiment, the end of the capsule opposite the delivery end is closed with a hemispherical end cap 12 to which the wing is integrally connected. The hemispherical exterior surface of the cap provides the required curved surfaces.

Referring to FIG. 7, the forward end of the barrel or tube 16 has a circumferential tapered pilot opening 22 leading to grooves 24 adapted to receive and interlock with corresponding circumferential beads or ridges on the closure cap 12. Such a cap has a generally hemispherical end wall joined to a cylindrical portion 28 having preferably two external annular beads 30 adapted to enter through the tapered pilot 22 of the barrel and engage in locked relation with the grooves 24 to mechanically secure the cap 12 to the body. Generally the use of a double bead securely seals the cap 12 onto the body thus preventing leakage of liquid into the capsule. A good seal also prevents the silicon lubricant from escaping from the device during packaging, storage or shipment. The cap 12 further contains a sealing ring or integral ridge 31 preferably between the beads (not shown in FIG. 7, see FIGS. 9 and 10). In one embodiment, the seal is triangular in cross section and smaller in height than the annular beads 30. The barrel or tube 16 contains an administrative charge in the form of a pre-formed cylindrical core 32 which, as formed and as shown in FIG. 1, has a rounded end face 34 adapted to make initial sealing engagement with the inner face 19 of the barrel. In FIG. 7, the rear or delivery end of the core 32 is shown in a condition it takes during use, in which the core end has been weakened by absorption of ruminal fluid and pressed toward the delivery opening 20 and against the end wall or end 18. Desirably, the hemispherical end wall of the cap 12 is formed internally with a pair of cross ribs 40 which form a flat seat for the opposite end of the spring 38.

The retention wing 14 is integrally connected and attached to the cap 12 adjacent the axis of the capsule body at the outermost central portion of the hemispherical wall 26 by a connection 42 over an area which lies on and close to the axis of the capsule. The wing 14 is substantially tangent to the hemispherical cap 12 on that central axis and has arms 44 extending outward in opposite directions from that point of attachment, as shown in FIGS. 1 and 3. Thus, in the illustrated embodiment the arms describe an angle of 90° with respect to the axis of the body. To reduce stress on the arms, each arm should lie within an angular space between 75° and 90° with respect to the body. The arms are adapted to be resiliently bent downward along the curved hemispherical outer surface of the cap 12 and to be brought substantially flat against the wall of the barrel or tube, so as to present a cross section of effective diameter not much larger than the barrel itself when the capsule is conditioned for insertion through the oesophagus into the rumen of an animal. When the capsule passes from the oesophagus into the rumen, the arms 44 of the wing 14 spring outward to their fully extended positions so as to block passage of the capsule back through the oesophagus and thus to retain the capsule against regurgitation or passage from the rumen.

The outstanding, substantially right-angular position of the wing arms 44 is considered advantageous both in preventing regurgitation of the capsule and to reduce bending and stress of the arms in the rumen, in that in a right-angular T-shape, the capsule is less likely than would be the case with other configurations to have its arms bent relative to each other or the barrel. More especially, such contractions and working are less likely to bend both arms to a position which would allow the forward end of the capsule to enter the oesophagus.

The wing 14 is desirably reinforced and made so that its arms 44 bend more easily back toward and against the sides of the capsule than forward in the opposition direction, away from the capsule, as would be required for the capsule to pass rear or delivery end first back through the oesophagus. In some cases, the wing as moulded takes a slightly arched shape so that its arms 44 are arched rearward toward the capsule, and hence so that less bending is required to bring them against the side of the capsule than to swing them in the opposite direction to a corresponding position.

The central portion of the wing is reinforced and desirably made of asymmetric cross section to increase the resistance of the wing to bending of its arms in a forward direction. As shown, an asymmetric configuration is obtained by forming longitudinal ribs on the outer surface of the wing. Thus, as shown in FIGS. 3–6, the basic cross section of the wing is that of a leaf spring in the form of a wide flat rectangle as shown in FIG. 4. Inward of FIG. 4, as shown in FIG. 5, the wing is formed with two upstanding side ribs 46 along its edges which extend over a substantial portion of its length along the barrel or tube 16 of the capsule. Still further inward, the wing is formed with a shorter central rib 48 which extends across the area 42 of attachment of the wing to the wall 26 of the cap. The central rib 48 is desirably of a length to extend substantially to the base of the hemispherical wall 26 when the arms are bent to insertion position, as shown in FIG. 8. The ribs 46 and 48 reinforce the wing 14 against forward bending, and thus give the wing greater resistance to forward bending than to the rearward bending which is required to carry its arms against the sides of the capsule barrel 16.

In a particular embodiment, a capsule for use in cattle comprised a barrel approximately 145.2 mm long and 33.35 mm in outside diameter, and a wing 12.9 mm wide and 162.5 mm long with side ribs 46 extending over 90% of the length of the wing and a centre rib 48 half the length of the side ribs, the wing being attached to the cap over a circular area having a diameter of about 11.2 mm.

This configuration and construction of the wing and its interrelation with the curved capsule end formed by the hemispherical wall 26 not only facilitates insertion of the capsule through the oesophagus and retention of the capsule through the rumen, but also enhances the ability of the capsule to withstand the conditions to which it is subjected in the rumen during its prolonged stay. In the rumen, the capsule and wing are subjected not only to chemical and biological conditions which it must withstand, but also to continuing and forceful mechanical stresses from the undigested food in the rumen and the movements of the rumen during the normal course of entrance, regurgitation, and digestion.

In a preferred embodiment a protrusion 50 is located on each arm of the wing 14 on the side adjacent the cap. A pair of protrusions 50 is positioned on the arms so that when the wing 14 is bent to insertion position, as shown in FIG. 8, the protrusions 50 are in contact with a portion of the curved surface on the hemispherical wall 26.

In our embodiment, the inner wall 27 of the cap 12 contains 2 grooves 52 (FIG. 7). These two grooves 52 reduce the thickness of the inner wall 27 to provide penetrable windows 51. The windows 51 are positioned adjacent to the protrusions 50 when the protrusions 50 come into contact with the curved surface of the wall 26. The protrusions penetrate the windows to provide a vent.

The capsule shown is readily assembled by inserting a pre-formed cylindrical core or composition 32 into the barrel or tube 16 of the body portion 10, inserting a piston 36 and spring 38 behind the capsule, and compressing the spring and pressing a cap 12 into the open end of the barrel 16 so that the annular beads 30 of the cap interlock in a snapping fashion with the grooves 24 of the barrel to provide a double engagement.

Before such assembly, a lubricant such as a light silicone lubricant is desirably applied either to the inner surface of the barrel or tube 16 or to the outer surface of the core 32. Such lubricant provides an initial seal, give some waterproofing for the pre-formed core, and forms a barrier film to prevent adhesion of the core to the barrel. This will help to ensure that the core 32 will slide in the barrel and will be initially pressed by the light spring 38 into sealing engagement with the end wall or end 18 and maintained in engagement therewith throughout the long period of sustained release of the capsule composition at the delivery opening 20 of the capsule.

The body 10 and cap 12 of the capsule are both adapted to be readily and inexpensively moulded from plastic material. Such material must, of course, be acceptable in the rumen of the living animal, and must be capable of resisting the chemical, biological, and physical conditions encountered in the rumen. Polymers of polyethylene and polypropylene, or preferably, of polypropylene itself, are suitable materials.

The capsule is conveniently moulded of two parts, with one part including the barrel and the delivery opening and defining an inside surface of uniform cross section to receive a capsule with predetermined clearance and to slidably receive the piston, and with the other part formed as a cap or closure for the forward end of the capsule and carrying the wing as an integral part of the moulding.

In some instances, capsules may need to remain in the rumen for extended periods of time, since in some parts of the world cattle remain on the range for such periods, and capsules may be administered periodically over that period. Cattle to which capsules are administered may have weights of upward from 200 kg, and in such animals the rumen may have a volume of over 100 liters, so that the presence of capsules of the size here contemplated can be tolerated in plural numbers and over long periods.

Insertion of a capsule into the rumen in cattle is conveniently done with an administration tool as shown in FIG. 8. Such tool comprises a tubular barrel 60 having an open end adapted to receive a capsule 8 with its wing arms 44 folded against the sides of its barrel 16. In this position the protrusions 50 engage the windows 51 and act as a seal to prevent the entry of water or ruminal contents. The barrel 60 is mounted on a tube 62 having a handle portion 64 by which the barrel can be manipulated through the mouth of the animal to place the end of the capsule 8 in the oesophagus. The tube 64 contains a thrust rod or cable 66 having a plunger 68 at its forward end and a thrust knob 70 at its outer end by which the plunger head 68 can be advanced to discharge the capsule 10 from the barrel 60 into the oesophagus. When the capsule with its folded arms 44 is thus discharged part way into the oesophagus, the capsule will then move on through the oesophagus into the rumen, and the oesophagus will hold the arms 44 in folded position until the capsule reaches the rumen. The arms will then spring outward to their normal outstanding position shown in full lines in FIG. 1 so as to retain the capsule in the rumen and exposing the vents.

When the arms 44 of the wing 14 are bent to folded positions, as indicated in dotted lines in FIG. 1, such arms bend in an arc on a long radius, in the clearance provided by and following the curved outer surface of the hemispherical wall 26 of the capsule so as not to be stressed to a point of strain, and when the arms are released from their folded position in the rumen, they tend strongly to return to their outstanding positions in diametrically opposite directions from the axis of the capsule, preferably with a slight arch as shown in FIG. 1. In such position, the wing presents a substantially flat outer face which tends to prevent the forward end of the capsule from entering the oesophagus to be regurgitated from the rumen. If the opposite end of the capsule should enter the rumen, the outspread wing and its high resistance to bending in the opposite direction will prevent the capsule from passing through the oesophagus and will thus prevent its regurgitation in that position. Further, the outspread arms 44 of the wing are so widely spaced angularly from each other and from the capsule that the working of the rumen has little tendency to bend the arms toward the capsule, and they are not so readily squeezed toward the capsule as arms at an acute angle to each other and to the barrel.

When a pre-formed core or composition 32 is first inserted in the barrel or tube 16, the spring 38 presses its end edge into sealing engagement with the end wall or end 18 of the barrel so as to limit contact of the ruminal fluid to the end face 34 of the core. In normal operation, such ruminal fluid migrates into the end of the core 32 and tends to soften and weaken it, and the core is then urged by the spring 38 toward the opening 20 in the end wall of the capsule. The capsule is thus held in sealed relation with the end wall 18 over a wide area as shown in FIG. 7, and the area of access to ruminal fluid to the end of the capsule 32 is limited by the size of the opening 20. Over that access area, the composition of the capsule 32 will be discharged to the ruminal fluid, as by washing, erosion, and dissolution. Meanwhile, the migration of ruminal fluid, or components thereof, into the end portion of the core will progress to maintain an equilibrium of softened material at the end of the core, which will be maintained by progressive movement of the core toward the discharge opening by the spring 38. This will produce a sustained administration of medicaments contained in the core to the rumen over a prolonged period. The rate of such administration will depend in part on the composition of the core 32, but will also be controlled in an important respect by the configuration of the end wall 18 of the capsule, as here shown and described, and especially by the outward-converging conical portion 17 thereof. The size of the opening 20 and the width and depth of the conical face 17 may be changed to vary the rate of administration.

Figure 12:
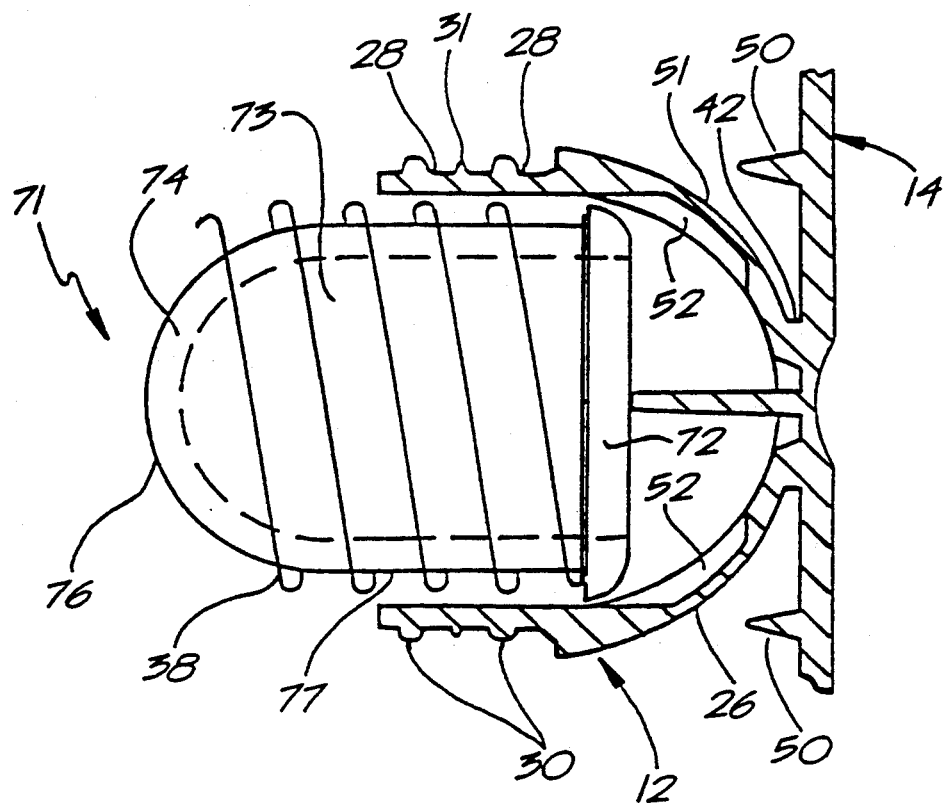
FIG. 12 is a side view of a thimble which can be used to prevent twisting of the spring.
Figure 13:
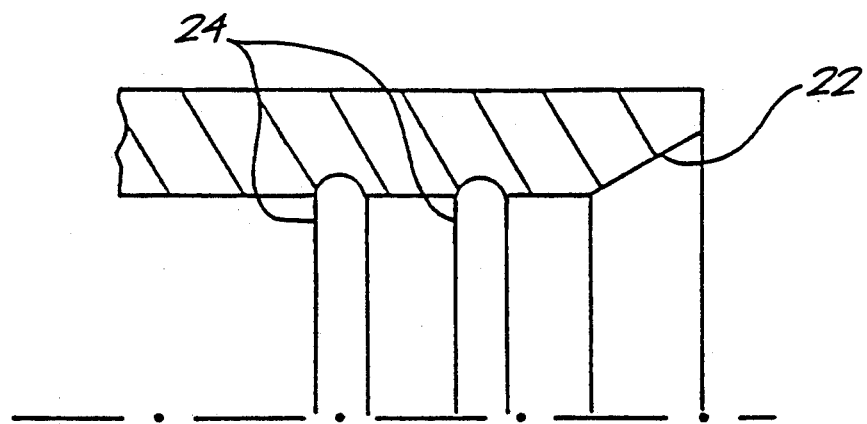
FIG. 13 is a section of the barrel taken along the centre line showing the tapered pilot.

As shown in FIG. 12, a thimble 71 adapted to be received within spring 38 is depicted in FIG. 12. Rim 72 separates the end of the spring from the cross ribs 40. At the same time, rim 72 aids in preventing the spring coils from transferring laterally and facilitates ease of assembly. The thimble has a cylindrical centre portion 75 and a rounded tip 76. This overcomes the problem of spring 38 fouling with cap 12 or side wall 37 of piston 36. Accordingly the spring 38 will coil onto the thimble and will not be caught between the cap 12 and barrel or tube 16 during assembly, especially by automated fabrication. In FIG. 12, the thimble 71 has a cavity 73, rim 72 and wall 74. In one method, the thimble 71 is inserted into the spring 38 and then both are inserted into the pre-lubricated tube 16 in which the core or composition 32 and piston 36 have already been situated. In this way, the cap 12 can be snapped on without fouling.

It is desirable to protect the sides and rear end of the core 32 in the capsule from contact with ruminal fluid which might tend to cause it to swell excessively against the sides of the barrel and prevent forward movement of the core 32 toward the end wall 18 to maintain sealing contact at that point. In FIG. 11, the piston 36 is formed with a flat end 35 and a cylindrical side wall 37 which has a plurality of grooves 53 along the circumference of the outer wall 37 of the piston. The lubricant is trapped within the grooves and provides a seal along the inside of the barrel as the material of the core 32 is consumed and so as to maintain the core in continuing sealing engagement with the end wall 18 of the barrel. With the use of such a labyrinth-style piston 36, the displacement or spring chamber behind the piston will not be sealed by the piston, and hence is desirably sealed against entrance of ruminal fluid.

With a sealed capsule, there are indications that the active agent contained in the core or charge of composition may be delivered to the animal in an initial surge or pulse and that the rate of administration then decreases and remains substantially constant over a prolonged period. It is not known why this initial pulse occurs, but it is believed that it may in part result from an initial increase in pressure in the spring chamber. Such increase could be caused by the change in temperature from an ambient temperature to a ruminal temperature of about 39° C. A pressure increase could also be caused by a higher rate of diffusion through the walls of the capsule of gases such as carbon dioxide from the rumen into the capsule than the rate of diffusion of nitrogen outward from the air contained in the spring chamber.

The capsule can be adapted for use in smaller animals, particularly in sheep.

In a particular embodiment of a capsule for use in sheep, the capsule had an overall length of 95.3 mm and a diameter of 18 mm, and carried a wing having a length of approximately 105 mm with a cross section of 6 mm by 1 mm. The end opening in the barrel has a diameter of 6 mm. The wing is attached to the cap over a central circular area having a diameter slightly greater than the width of the wing.

The smaller sheep capsule is administered to sheep in a manner analogous to the administration of the cattle capsule, and acts in an analogous manner. While the wing of the smaller sheep capsule is of uniform cross section throughout its length and not reinforced with ribs nor bowed as in the cattle capsule, the sheep capsule has been used successfully and has been found to be retained in the sheep rumen for prolonged periods.

The following formulation examples illustrate typical solid therapeutic compositions which can be included in the sustained release capsules.

EXAMPLE 1

A typical formulation contains:
Teric 12A23: 50%
Monensin: 40%
Glycerol ester: 10%.

Formulations are melted and moulded into a suitable shaped core to fit the band of the device.

After cooling, cores are placed into the plastic body, a piston and spring is added and the cap is rammed onto the body. The process is carried out in an automatic machine designed for the complete assembly of the device.

EXAMPLE 2

If an anti foam agent is included a typical formulation is:
Gensil 800: 10%
Monensin: 40%
Glycerol ester: 50%.

The formulation is prepared according to the procedure of Example 1.

EXAMPLE 3

A typical formulation contains:
Teric 12A23: 30%
Narasin: 40%
Glycerol ester: 30%.

The formulation is prepared according to the procedure of Example 1.

EXAMPLE 4

If an anti foam agent is included a typical formulation is:
Silbione 70451: 20%
Salinomycin: 30%
Glycerol ester: 50%.

The formulation is prepared according to the procedure of Example 1.

EXAMPLE 5

A typical formulation contains:
Silbione ®70 451: 20%
Teric ®12A23: 40%
Avoparcin: 20%
Glycerol ester: 20%.

The formulation is prepared according to the procedure of Example 1.

EXAMPLE 6

If an anti foam agent is included a typical formulation is:
Silbione ®70 451: 20%
Vancomycin: 40%
Glyceryl monolaurate: 40%.

The formulation is prepared according to the procedure of Example 1.

EXAMPLE 7

A typical formulation contains:
Teric ®12A23: 40%
Mebendazole: 20%
Glycerol ester: 40%.

The formulation is prepared according to the procedure of Example 1.

EXAMPLE 8

If an anti foam agent is included a typical formulation is:
    Gensil ®800: 20%
    Pyrantel pamoate: 20%
    Sorbitan monostearate: 60%.

The formulation is prepared according to the procedure of Example 1.

EXAMPLE 9

A typical formulation contains:
    Teric 12A23: 20%
    Avermectin: 20%
    Glycerol ester: 60%.

The formulation is prepared according to the procedure of Example 1.

EXAMPLE 10

If an anti foam agent is included a typical formulation is:
    Gensil 800: 20%
    Levamisole: 20%
    Glycerol ester: 60%.

The formulation is prepared according to the procedure of Example 1.

EXAMPLE 11

A typical formulation contains:
    Monensin: 70%
    Glycerol ester: 30%.

The Monensin is melted and moulded into a suitable shaped core to fit the band of the device.

After cooling, cores are placed into the plastic body, a piston and spring is added and the cap is rammed onto the body. The process is carried out in an automatic machine designed for the complete assembly of the device.

EXAMPLE 12

If an anti foam agent is included a typical formulation is:
    Gensil 800: 20%
    Monensin: 40%
    Glycerol monostearate: 40%

The formulation is prepared according to the procedure of Example 1.

INDUSTRIAL APPLICABILITY

A sustained release capsule of the invention can be readily utilised in ruminant animals to provide a more efficient release of therapeutic composition, a capsule which is easier to manufacture and which is less likely to leak during storage, shipment and packaging.

What we claim is:

1. A sustained release capsule adapted to be inserted into the rumen of a ruminant animal through its oesophagus and retained within the rumen over a prolonged period to continuously deliver a biologically active composition carried in the capsule, comprising an elongated tubular body comprising a tube and an end cap secured to one end thereof for substantially enclosing the biologically active composition, the other end of the capsule being a delivery end, the body having an opening at the delivery end of the capsule for delivery of the composition to the rumen, and a plurality of retention arms attached to or formed integrally with the cap, the arms being adapted to extend outwardly from the cap for retaining the capsule in the rumen, the arms being resilient to enable them to bend from their outwardly extending positions toward the body so that they lie alongside the body allowing the capsule to be inserted through the animal's oesophagus, said cap having at least one area of reduced thickness and said arms having at least one protrusion on the side adjacent the cap corresponding so that when the arms are urged along side said body, the protrusion(s) engage and cause rupture(s) of the wall of the cap at said at least one area thereby providing at least one vent to relieve any vacuum formed on movement of said piston, said arms being adapted to return to their normal outwardly extending positions when the capsule reaches the rumen, the cap and tube each having cylindrical portions which nest one within the other to form a sealed closure, one of the portions having spaced apart annular grooves formed therein, the other cylindrical portion having similarly spaced apart circumferential beads which fit within the grooves, one of the portions also comprising a circumferential sealing ring.

2. The sustained release capsule of claim 1, wherein the sealing ring is located between the grooves and the beads.

3. The sustained release capsule of claim 1, wherein one of the cylindrical portions is larger in diameter than the other and the larger portion is provided with a tapered pilot opening.

4. The sustained release capsule of claim 3, wherein the cylindrical portion of the tube is larger in diameter than the cylindrical portion of the cap, the cylindrical portion of the tube having the grooves formed therein.

5. The sustained release capsule of claim 4, wherein the sealing ring further comprises an integral ridge formed on the cylindrical portion of the cap.

6. The sustained release capsule of claim 1, wherein said arms are reinforced.

7. The sustained release capsule of claim 1, wherein the cap has a hemispherical portion, each arm being integrally formed on the hemispherical portion, each protrusion being located near a point of attachment of the arm and the hemispherical portion.

8. The sustained release capsule of claim 1 and which further includes a piston, a coil spring and a thimble having a rim, the piston being located within the body, the piston urged toward the discharge opening by the coil spring, one end of the spring impinging onto the piston, the other end of the spring impinging on the rim of the thimble, the thimble comprising a cylindrical centre portion, tapered at one end and having the rim formed around the other end, the tapered end of the thimble inserted into the spring and having the rim interposed between the spring and the end cap.

9. A sustained release capsule in accordance with claim 1 wherein the tubular body contains a labyrinth piston surrounded by lubricant and means for biasing the piston toward the delivery end for moving a supply of active composition toward the delivery opening when the capsule is in use.

10. A sustained release capsule in accordance with claim 9 wherein the piston is adapted to move in slidable sealed relation in the body to restrict access of ruminal fluid to the supply of active composition other than at the delivery opening.

11. A sustained release capsule in accordance with claim 1 wherein the arms are formed to have relatively less resistance to bending from their outwardly extending positions toward the delivery end of the capsule to positions in which they lie against the body of the capsule, and relatively more resistance to bending away from the delivery end.

12. A sustained release capsule in accordance with claim 11 wherein the arms are of asymmetric cross section to control their resistance to bending.

13. A sustained release capsule in accordance with claim 11 wherein resistance of the arms to bending away from the delivery end is increased by providing the arms with one or more longitudinal reinforcing ribs on each arm, the ribs being disposed on each arm facing away from the delivery end of the capsule.

14. A sustained release capsule in accordance with claim 1 wherein the capsule has at least one pair of arms that are substantially continuous so as to form a wing extending across the end of the capsule.

15. A sustained release capsule in accordance with claim 9 wherein said biasing means is a coil spring.

16. A sustained release capsule in accordance with claim 15 wherein said spring is coiled around a thimble.

17. A sustained release capsule in accordance with claim 1 wherein the biologically active composition comprises a polyether antibiotic, a glycopeptide antibiotic, an anthelmintic and/or an endectoparasiticide.

18. A sustained release capsule in accordance with claim 17 wherein said polyether antibiotic is monensin, narasin, lasalocid, salinomycin, ionomycin, laidlomycin, nigericin, grisorixin, dianemycin, lenoremycin, lonomycin, antibiotic X206, alborixin, septamycin, antibiotic A204, etheromycin, mutalomycin, K41, isolasalocid A, lysocellin, tetronasin, antibiotic X-14766A, antibiotic A23187, or antibiotic A32887.

19. A sustained release capsule in accordance with claim 17 wherein said glycopeptide antibiotic is actaplanin, avoparcin, A35512, A477, ristocetin, or vancomycin.

20. A sustained release capsule in accordance with claim 17 wherein said anthelmintic is antimony potassium tartrate, bephenium hydroxy naphthoate, bithionol, chloroquine, dichlorophen, diethylcarbamazine citrate, hexylresorcinol, hycanthone mesylate, lucanthone hydrochloride, mebendazole, niclosamide, niridazole, piperazine citrate, pyrantel pamoate, pyrvinium pamoate, quinacrine hydrochloride, stibocaptate, stibophen, tetrachloroethylene, thiabendazole, phenothiazine, hexachloroethane, carbon disulphide, or benzimidazole.

21. A sustained release capsule in accordance with claim 17 wherein said endectoparasiticide is organo phosphate, carbamate, avermectin, levamisole, or sodium thiacetarsamide.

22. A sustained release capsule in accordance with claim 17 further comprising a surfactant.

23. A sustained release capsule in accordance with claim 22 wherein said surfactant is an octyl ethoxylate, nonyl ethoxylate, dodecyl phenol ethoxylate, natural alcohol ethoxylate, synthetic alcohol ethoxylate, saturated fatty acid ethoxylate, unsaturated fatty acid ethoxylate, block copolymer ethoxylate, or random copolymer ethoxylate.

24. A sustained release capsule in accordance with claim 23 wherein said alcohol ethoxylate is Teric 12A23.

25. A sustained release capsule in accordance with claim 17 further comprising an anti foam agent.

26. A sustained release capsule in accordance with claim 25 wherein said anti foam agent is dimethyl silicon, Gensil 800, or Silbione 70 451.

27. A sustained release capsule in accordance with claim 1 containing a solid core of the biologically active composition.

28. The sustained release capsule of claim 1 in which the resilient arms normally extend from the body at an angle between 75° and 90° with respect to the axis of the tubular body.

29. The sustained release capsule of claim 1 in which for each arm said cap has an external curved surface disposed with respect to the arm so that when the arm is bent toward the body, the arm contacts the curved surface and the curved surface controls the bending of the arms so that the arm does not bend improperly.

* * * * *